United States Patent [19]

Steinberg et al.

[11] Patent Number: 5,767,165
[45] Date of Patent: Jun. 16, 1998

[54] METHOD FOR CONVERTING NATURAL GAS AND CARBON DIOXIDE TO METHANOL AND REDUCING $CO_2$ EMISSIONS

[76] Inventors: Meyer Steinberg, 15 Alderfield La., Melville, N.Y. 11747; Yuanji Dong, 101-1A Springset Dr., Cary, N.C. 27513

[21] Appl. No.: 583,315

[22] Filed: Jan. 5, 1996

Related U.S. Application Data

[63] Continuation-in-part of Ser. No. 405,032, Mar. 16, 1995, abandoned.
[51] Int. Cl.$^6$ ................................................ C07C 27/06
[52] U.S. Cl. .................... 518/703; 518/702; 518/704; 518/705; 423/453; 423/458
[58] Field of Search .................................. 518/702, 703, 518/704, 705; 423/453, 458

[56] References Cited

U.S. PATENT DOCUMENTS

| | | |
|---|---|---|
| 1,803,221 | 4/1931 | Tyrer et al. |
| 5,529,599 | 6/1996 | Calderon .................... 75/10.63 |

OTHER PUBLICATIONS

Kirk–Othmer Encyclopedia of Chemical Technology, vol. 12, p. 965, 1978.
Kirk–Othmer Encyclopedia of Chemical Technology, vol. 15, p. 400, 1978.

*Primary Examiner*—Gary Geist
*Assistant Examiner*—S. Padmanabhan
*Attorney, Agent, or Firm*—Kelly & Hulme, P.C.

[57] ABSTRACT

A process for the production of methanol from natural gas containing methane comprising the thermal decomposition of methane and the subsequent reaction of the resulting hydrogen gas with carbon dioxide in a catalyst containing methanol synthesis reactor to produce methanol. Alternative methods include the gasification with carbon dioxide of at least a portion of the carbon produced by the decomposing step, to produce carbon monoxide, which is then reacted with hydrogen gas to produce methanol; or the reforming of a portion of the natural gas feedstock used in the decomposing step with carbon dioxide to produce carbon monoxide and hydrogen gas, which carbon monoxide and hydrogen are then combined with additional hydrogen from the natural gas decomposing step in a methanol synthesis reactor to produce methanol. The methods taught reduce the overall amount of carbon dioxide resulting from the methanol production process.

2 Claims, 2 Drawing Sheets

METHOD FOR CONVERTING NATURAL GAS AND CARBON DIOXIDE TO METHANOL AND REDUCING CO₂ EMISSIONS

This application is a continuation-in-part of application Ser. No. 08/405,302 filed Mar. 16, 1995, abandoned.

BACKGROUND OF THE INVENTION

1. Field of the Invention

The present invention is related to a method for the production of methanol, and more specifically, to a method for production of methanol by conversion of natural gas and carbon dioxide which method has reduced carbon dioxide emissions.

2. Description of the Prior Art

Methanol, which was first discovered in the late 1600's, has found use as a chemical feedstock and as an efficient fuel. Its earliest and largest use to date is as a feedstock in the production of formaldehyde. While in recent years such use has decreased, methanol has found increasing use in the production of such materials as acetic acid and methyl tert-butyl ether (MTBE—a gasoline additive). In addition, methanol is being used directly (with increasing demand) as a fuel in race cars, in farm equipment and, in some areas, as a general purpose automotive fuel. Methanol is fast becoming an environmentally preferred alternative transportation fuel and can also serve as a clean stationary power plant fuel.

There are several commercially viable methods of producing methanol. These methods include:

1. The steam reforming of natural gas in accordance with the following reaction:

$$CH_4 + H_2O \rightarrow CO + 3H_2 \quad (1)$$

2. The gasification of natural gas with carbon dioxide in accordance with the following reaction:

$$CO_2 + CH_4 \rightarrow 2CO + 2H_2 \quad (2)$$

or a combination of these methods.

As is clear to those skilled in the art the goal of each of these conventional methods is to produce or otherwise provide carbon monoxide and hydrogen in a molar ratio of 1 mole of CO to 2 moles of $H_2$. These reactants are then reacted in a methanol synthesis reactor in the presence of a catalyst to produce methanol in accordance with the following exothermic reaction:

$$CO + 2H_2 \rightarrow CH_3OH \quad (3)$$

The processes known in the art often produce carbon dioxide which, if fed to the methanol synthesis reactor, results in a lower methanol yielding reaction which competes with the above reaction for the valuable hydrogen as follows:

$$CO2 + 3H_2 \rightarrow CH_3OH + H_2O \quad (4)$$

(A more detailed discussion of the above processes can be found in *Kirk-Othmer Encyclopedia of Chemical Technology*, Vol. 15, pp 398–415 John Wiley & Sons (1978).)

Therefore, carbon dioxide must be removed prior to entry into the methanol synthesis reactor. This obviously adds additional complexity, and, therefore expense to the process. In addition, the creation and/or emission of carbon dioxide by the methanol forming process creates other problems since carbon dioxide is a green house gas, the negative effects of which are only beginning to be understood. What is well understood, however, is the desire to reduce or eliminate carbon dioxide production and processes which reduce such emissions or in fact consume carbon dioxide as part of the process are desirable.

It is therefore an object of the present invention to provide an efficient method for the production of methanol from natural gas and carbon dioxide.

It is another object of the present invention to provide a method which produces a high yield of methanol per unit feedstock.

It is yet another object to the present invention to provide a method for the production of methanol having reduced carbon dioxide emissions. It is another object of the present invention to utilize waste $CO_2$ from coal burning power plants and other sources to produce methanol to reduce overall net $CO_2$ emissions.

It is another object of the present invention to produce carbon as a co-product to the production of methanol.

The above and other objects and advantages of the present invention will become apparent from the following specification read in conjunction with the annexed drawings.

SUMMARY OF THE INVENTION

This invention relates to the production of methanol by conversion of natural gas (which is comprised mainly of methane) and carbon dioxide. The process of the present invention is comprised of two (2) basic steps, the thermal decomposition of methane (natural gas) to produce elemental carbon and hydrogen gas followed by the catalyzed reaction of the hydrogen gas produced in step one of the process with carbon dioxide in a methanol synthesis reactor to produce a gas stream containing methanol. The methanol may then be separated from the gas stream by known techniques. The carbon is separated as a co-product of the process.

As shown above and described in more detail below, the process of the present invention consumes a substantial amount of carbon dioxide. The source of the carbon dioxide used in the present invention may be any sources. However, since as indicated above the net creation and/or emission of carbon dioxide is something to be reduced or avoided, the process of the present invention may be most advantageously operated in conjunction with a carbon dioxide producing process such as a fossil fuel fired energy producing plant (i.e., e.g., a coal fired electrical generation plant or waste incinerators). As is well known in the art such fossil fuel fired plants produce carbon dioxide as well as other gases which, if they are not otherwise dealt with, are discharged to the air, having many negative impacts on the environment such as global warming. However, such a plant operated in conjunction with the present invention could result in reduced carbon dioxide emissions since a substantial portion of the carbon dioxide generated could be consumed in the process of the present invention.

In addition, as indicated above, the process of the present invention has the added feature of producing elemental carbon. The carbon which is removed from the thermal decomposition step may be stored, sold or employed in other processes where elemental carbon is of value such as the production of carbon black.

An alternate embodiment of the present invention involves the additional step of gasification of a portion of the elemental carbon produced in step one with carbon dioxide to produce carbon monoxide and thereafter reacting the hydrogen produced in the natural gas thermal decomposition step with the carbon monoxide in a catalyized reaction in a methanol synthesis reactor to form methanol.

A third embodiment of the present invention involves the step of reforming a portion of the natural gas feedstock with carbon dioxide to produce carbon monoxide and hydrogen which constituents are then provided to a methanol synthesis reactor along with the hydrogen gas produced in the methane decomposition step, where the carbon monoxide and hydrogen are combined in a catalyzed reaction to produce methanol.

It will be clear to those skilled in the art that the thermal energy necessary to cause the thermal decomposition of the natural gas in step one in the above described process may be provided in any of the known manners, but it is most commonly provided by the combustion of natural gas in accordance with the following reaction:

$$2CH_4 + 4O_2 \rightarrow CO_2 + 4H_2O \tag{5}$$

As can be seen this reaction produces carbon dioxide. However, since the process of the present invention also consumes carbon dioxide and in fact does so in an amount greater than that produced by the above reaction 5, the use of the present process results in the reduction of carbon dioxide produced by the methanol producing process. In addition, if hydrogen gas produced by methane decomposition is substituted as the fuel in the process or if an alternative non-fossil fuel method of supplying thermal energy (e.g. solar energy or nuclear energy to the methane decomposition reactor is employed, for the decomposition step, the production of carbon dioxide in the process of the present invention is further reduced.

The carbon produced in the process is either sequestered or used as a materials commodity and is not burned as fuel.

When methanol is used as an alternative transportation fuel in automotive engines or as a clean stationary power plant fuel, the methanol combustion reaction is as follows:

$$CH_3OH + 3/2O_2 \rightarrow CO_2 + 2H_2O \tag{6}$$

As indicated, carbon dioxide is produced. However, since carbon dioxide recovered from a fossil fuel burning power plant is used in the synthesis of methanol according to reaction (4) above, the net carbon dioxide produced in the system becomes near zero when methane is used as a fuel to heat the methane decomposition reaction of step one of the process or is zero when hydrogen is used as a fuel.

DETAILED DESCRIPTION OF THE PRESENT INVENTION

Figure 1:
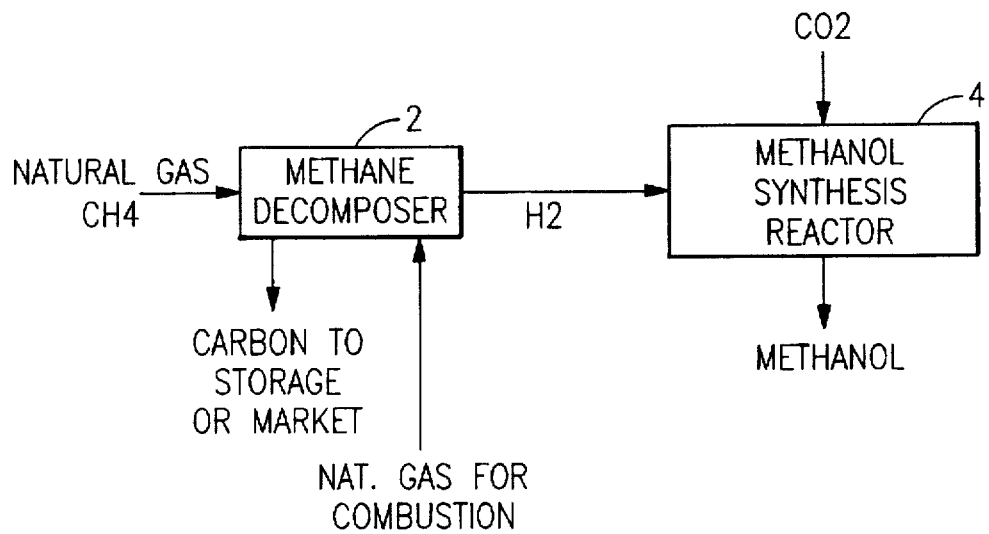
FIG. 1 is a simplified schematic process flow chart of the process of the present invention.

Referring to FIG. 1, an embodiment of the overall process is shown which may be divided into two principal sections: thermal decomposition, and methanol synthesis.

As shown, in the thermal decomposition step, methane ($CH_4$) is fed into the methane decomposition reactor (MDR)

2. This thermal decomposition step yields elemental carbon (in solid form) and large amounts of hydrogen gas and is described by the following reaction:

$$3CH_4 \rightarrow 3C + 6H_2 \tag{7}$$

The carbon produced in this MDR 2 is removed for other use or sale.

In the second step of the process, the hydrogen gas produced in the MDR 2 is fed into the methanol synthesis reactor (MSR) 4 where it is combined with carbon dioxide in a catalyzed reaction to produce methanol as follows:

$$CO_2 + 3H_2 \rightarrow CH_3OH + H_2O \tag{8}$$

Methanol resulting from this process is synthesized from carbon dioxide and hydrogen, as detailed in reaction 8 above, rather than by the more conventional combination of hydrogen and carbon monoxide (in a 2:1 molar ratio).

Figure 2:
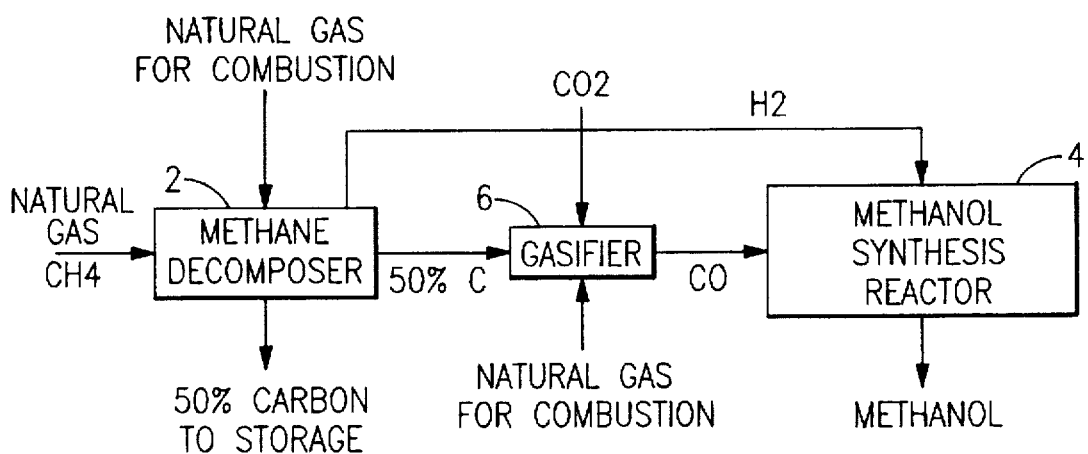
FIG. 2 is a schematic process flow chart showing an alternate embodiment of the present invention.

An alternate embodiment of the present invention is shown in FIG. 2. In this embodiment, a gasification step 6 is added between the methane decomposition step and the methanol synthesis step. In this additional step, a portion of the elemental carbon produced in the MDR 2 is reacted in the carbon gasification reactor 6 with carbon dioxide to produce carbon monoxide in accordance with the following reaction:

$$CO_2 + C \rightarrow 2CO \tag{9}$$

The carbon monoxide is then reacted with the hydrogen gas (in a ratio of 1 mole carbon monoxide and 2 moles hydrogen gas) produced in the MDR 2 to form methanol, as follows:

$$CO + 2H_2 \rightarrow CH_3OH \tag{10}$$

Figure 3:
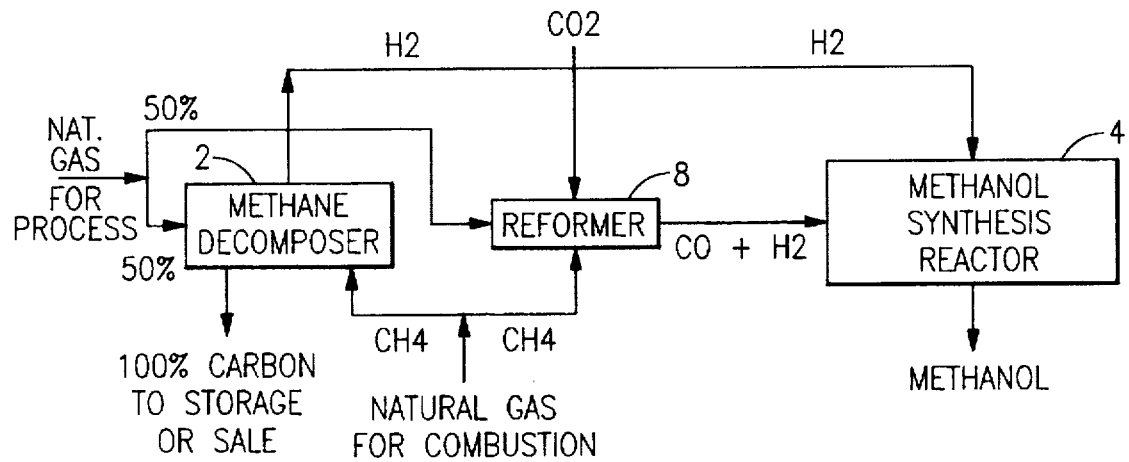
FIG. 3 is a schematic process flow sheet showing another alternate embodiment of the present invention.

In yet another embodiment of the present invention, as depicted in FIG. 3, the step of reforming a portion of the natural gas feedstock with carbon dioxide in a reforming reactor 8 is undertaken, the chemical reaction being as follows:

$$CH_4 + CO_2 \rightarrow 2CO + 2H_2 \tag{11}$$

The carbon monoxide and hydrogen produced in this step may then be combined with the hydrogen produced in the MDR 2 and fed into the MSR 4 wherein methanol is produced in accordance with the catalyzed reaction 10 above.

Figure 4:
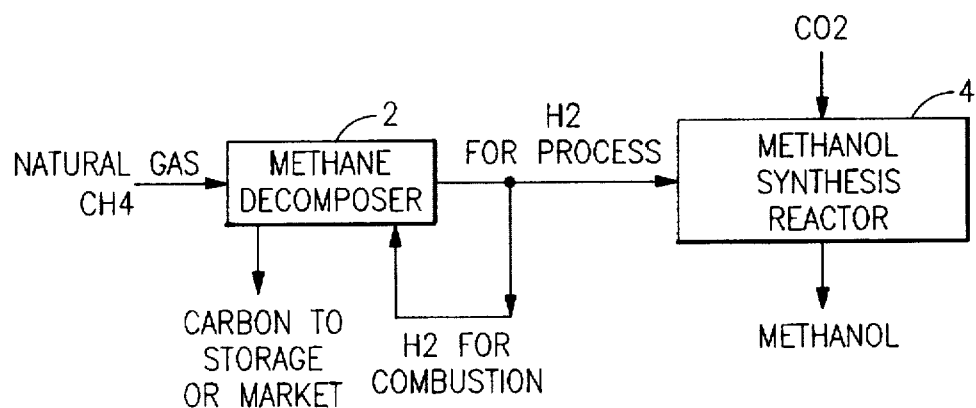
FIG. 4 is the schematic flow chart of FIG. 1 showing a hydrogen gas recycle stream.

Still another embodiment of the present invention is shown in FIG. 4. In this embodiment, a portion of the hydrogen produced in the MDR 2 is diverted for use as a fuel for providing the thermal energy required by the MDR 2. By eliminating the use of natural gas as the fuel, the amount of carbon dioxide produced by the overall process is reduced to zero. Furthermore, since the MDR 2 produces hydrogen in an amount in excess of that needed to supply the thermal energy for reaction 6 and the stoichiometric amount required by reaction 8 above (the reaction taking place in the MSR 4 in forming methanol) the $CO_2$ emissions is reduced to zero with a relatively small reduction in the methanol production of the entire process.

As indicated above, it is clear that there must be a source of thermal energy to cause the decomposition of the methane in the MDR 2. As also described above, this is most typically provided by burning methane or hydrogen gas. However, in accordance with the present invention, molten salts or molten metal technology may be used advantageously employed to decompose the methane into elemental carbon and hydrogen which molten metal/salt reactor can be used as the methane decomposition reactor.

It has been found that at an appropriate temperature, methane which may be bubbled through a bath of molten salt or metal will crack to carbon and hydrogen. Since the solid carbon has a density different from and less than the density of the molten material used to effectuate the cracking, it will float on the surface of the molten material and be able to be easier separated out from the reactor. In addition, the hydrogen gas produced by the cracking of the methane in this manner will bubble through the molten bath and can be drawn off the top of the reactor for use in the subsequent steps of the process of the present invention.

The advantage of this technique over the techniques known in the art is that the previously known techniques do not efficiently convert the methane contained in the natural gas feedstock to the component carbon and hydrogen gas, which reduces the overall conversion efficiency of the process described above. However, the use of the molten metal/salt technology results in a situation where virtually all of the methane that can be cracked at a given temperature and pressure is cracked to carbon and hydrogen gas.

The molten materials most advantageously employed herein include molten iron (Fe), molten tin (Sn) and molten salt (NaCL, NaF), with the iron or tin being preferred since the difference in density between the molten metals (iron and tin) and the carbon is greater than between the salt and carbon materials, thereby making the physical separation of the carbon from the molten material easier. In addition, it has been found that a molten material reactor operating at or greater than 800° C. and 1 to 10 atm. pressure results in almost complete decomposition of the methane of more than 90% into carbon and hydrogen gas.

As will be apparent to one skilled in the art, the various reactors advantageously used in association with this present invention are any of those reactors well known in the industry and are operated at temperatures and conditions also known and include but are not limited to low pressure methanol systhesis reactors, fluidized bed reactors, pyrolysis reactor, and the like.

The process of the present invention is illustrated by a process simulation computer model developed by the inventor using standard thermodynamic equilibrium data for the reactants used and is based on the following conditions:

1. The methane decomposition reactor (MDR) is designed to achieve near thermodynamic equilibrium at or greater than 800° C. and pressure of 1 atm. to 10 atm of pressure.

2. Energy for the MDR is obtained by the combustion of natural gas and/or hydrogen gas recycled from the methanol synthesis reactor (MSR).

3. The process gas from the MDR is compressed to 50 atm. prior to being fed into the MSR.

4. The carbon dioxide consumed in the MSR is recovered from a fossil fuel power plant and is mixed with a hydrogen prior to being fed into the MSR.

5. The MSR is operated in 50 atm. and 260° C.

Table 1 gives the data yielded by the computer simulation. The data given is based on a 100 kg. of methane as the feedstock and stoichiometric quantities of the other reactants.

A comparative analysis comparing conventional methanol production methods with the current invention was undertaken. The results of this analysis are given in Table 2.

As can be seen in Table 2, the processes of the present invention, greatly reduce the amount of carbon dioxide emissions typically found in methanol producing processes. While the price of this carbon dioxide emission reduction is a reduction in methanol production per unit of natural gas feedstock by conventional methods, the methanol reduction per unit of natural gas consumed may be a small price to pay when compared to the damage to the environment from carbon dioxide emissions. The cost offset for the methanol reduction can be compensated by the sale of the carbon coproduct from the process as a materials commodity.

TABLE 1

| UNIT | $CH_4$ FUEL FOR MDR | $H_2$-RICH GAS FUEL FOR MDR |
| --- | --- | --- |
| MDR | | |
| Pressure, atm | 1 | 1 |
| Temperature, °C. | 800 | 800 |
| $CH_4$ Feedstock, Kg | 100 | 100 |
| Preheat Temp, °C. | 550 | 640 |
| $CH_4$ Fuel for MDR, Kg | 2.7 | — |
| $CH_4$ Conversion, % | 91.9 | 91.9 |
| Carbon Produced, Kg | 68.8 | 68.8 |
| Heat Load, Kcal | 90,981 | 82,091 |
| Purge Gas for Fuel, Kmol | 2.5 | 2.4 |
| MSR | | |
| Pressure, atm | 50 | 50 |
| Temp., °C. | 260 | 260 |
| $CO_2$ Feedstock, Kg | 163.1 | 156.6 |
| $CO_2$ Conversion, % | 90.9 | 90.9 |
| Methanol Prod., Kg | 104.7 | 100.6 |
| Water Cond., Kg | 60.6 | 58.2 |
| Energy for Gas Compression To MSR | | |
| Energy, Kcal | 78,244 | 75,114 |
| Performance | | |
| Ratio Methanol/$CH_4$, Kg/Kg | 1.02 | 1.01 |
| Carbon Efficiency MeOH, % | 51.1 | 50.3 |
| Thermal Eff. MeOH, % | 41.7 | 41.1 |
| Thermal Eff. C + MeOH, % | 81.4 | 81.8 |
| $CO_2$ Emission, Lbs/MM BTU | 29.0 | 22.7 |
| $CO_2$ Emission, Kg/GJ | 12.6 | 9.8 |

TABLE 2

COMPARATIVE ANALYSIS FOR METHANOL PRODUCTION

| PROCESS | I. CONV. STEAM REF. | II. CONV. $CO_2$ REF. | III. CONV. STEAM AND $CO_2$ REF. | IV. Present Inv. $CO_2$ Gasif. | V. Present Inv. | IV. Present Inv. $H_2$ Recycle |
|---|---|---|---|---|---|---|
| Energy for process (Kcal/mol MeOH) | 60 | 45 | 45 | 39 | 27 | 31 |
| Yield MeOH MeOH/$CH_4$ (mol/mol) | 0.95 | 1.04 | 1.01 | 0.85 | 0.62 | 0.58 |
| $CO_2$ Emission (mol $CO_2$/mol MeOH) | 1.05 | 0.96 | 0.99 | 0.68 | 0.13 | 0.00 |
| Gasifier Shift or Reformer Reactor | YES | YES | NO | YES | NO | NO |
| Acid gas removal | NO | YES | NO | NO | NO | NO |
| Carbon yield Mol C/Mol MeOH | 0 | 0 | 0 | 0.5 | 1.5 | 1.73 |
| No. of Reactors | 2 | 4 | 2 | 3 | 2 | 2 |
| Percent $CO_2$ reduction from base % | BASE | −9 | −6 | 35 | 88 | 100 |

What is claimed:

1. A process for the production of methanol from methane containing natural gas comprised of:
   a. Thermally decomposing said methane to produce hydrogen gas and elemental carbon; wherein this decomposing step is comprised of:
      i. Bubbling the methane through a bath comprised of a molten material operating at a temperature of at least 800° C. and a pressure of 1 to 10 atm.;
      ii. cracking said methane through the use of said molten material such that elemental carbon and hydrogen gas are formed;
      iii. Removing the hydrogen gas from the top of the bath; and
      iv. collecting the elemental carbon off the top of the liquid surface of the bath; and
   b. Reacting said hydrogen gas with carbon dioxide in a methanol synthesis reactor in the presence of a catalyst to form a product containing methanol.

2. The process of claim 1 wherein the molten material is selected from the group comprising molten metal tin and molten metal iron.

* * * * *